United States Patent
Martin et al.

(10) Patent No.: US 7,759,114 B2
(45) Date of Patent: Jul. 20, 2010

(54) SENSOR CHIPS

(75) Inventors: Lisandra Lorraine Martin, Mt Eliza (AU); Daniel Luke Johnson, Unley (AU)

(73) Assignee: Tacnia Pty Ltd, Adelaide (AU)

( * ) Notice: Subject to any disclaimer, the term of this patent is extended or adjusted under 35 U.S.C. 154(b) by 750 days.

(21) Appl. No.: 11/327,660

(22) Filed: Jan. 6, 2006

(65) Prior Publication Data
US 2006/0194343 A1 Aug. 31, 2006

Related U.S. Application Data

(63) Continuation-in-part of application No. PCT/AU2004/000923, filed on Jul. 8, 2004.

(30) Foreign Application Priority Data
Jul. 8, 2003 (AU) .............................. 2003903504

(51) Int. Cl.
- *C12M 1/34* (2006.01)
- *G01N 33/53* (2006.01)
- *G01N 33/553* (2006.01)
- *G01N 33/24* (2006.01)

(52) U.S. Cl. ................... 435/287.2; 435/7.92; 436/525; 436/79; 436/80; 436/81; 514/836; 424/179.1

(58) Field of Classification Search ................ 436/534, 436/525, 532, 80, 81, 823; 530/402, 403; 568/21, 61, 69; 514/836; 424/179.1
See application file for complete search history.

(56) References Cited

U.S. PATENT DOCUMENTS
5,439,829 A 8/1995 Anderson et al.
(Continued)

FOREIGN PATENT DOCUMENTS
AU 2003903504 7/2003
(Continued)

OTHER PUBLICATIONS

Lindoy et al. Transition metal complexes of synthetic macrocyclic ligands. Chem. Soc. Rev. 1975, vol. 4, pp. 421-441.*

(Continued)

*Primary Examiner*—Shafiqul Haq
(74) *Attorney, Agent, or Firm*—Virtual Law Partners LLP; Richard G. A. Bone (57) ABSTRACT

A method for selectively orienting molecules on a surface of a solid support. The method includes the steps of: (a) attaching a linker molecule to the surface of the solid support, the linker molecule including a head group that is capable of binding to the solid support, and a tail group that is capable of chelating to a metal ion; (b) subsequently treating the solid support with a solution containing the metal ion; (c) attaching a metal ion chelating tag to the molecules to form tagged molecules; and (d) capturing the tagged molecules on the solid support by contacting it with the tagged molecules to form a monolayer of molecules on the surface of the solid support in which a majority of the molecules are held in the same orientation with respect to the surface. The invention also provides a sensor chip formed using the methods of the invention.

12 Claims, 5 Drawing Sheets

U.S. PATENT DOCUMENTS

| | | | |
|---|---|---|---|
| 5,834,224 | A | 11/1998 | Ruger et al. |
| 6,063,637 | A * | 5/2000 | Arnold et al. ................ 436/94 |
| 7,456,276 | B2 * | 11/2008 | Christensen et al. ..... 536/123.1 |
| 2002/0042074 | A1 | 4/2002 | Bamdad et al. |
| 2003/0032043 | A1 | 2/2003 | Pohl et al. |

FOREIGN PATENT DOCUMENTS

| | | |
|---|---|---|
| WO | WO 98/31839 | 7/1998 |
| WO | WO 00/47548 | 8/2000 |
| WO | WO 03/042249 | 5/2003 |
| WO | WO 2005/003383 | 1/2005 |

OTHER PUBLICATIONS

Allard, L., et al., "Versatile Method for Production and Controlled Polymer-Immobilization of Biologically Active Recombinant Proteins," *Biotechnology and Bioengineering*, 80(3):341-8, (2002).

Andreescu, S., et al., "Immobilization of Enzymes on Screen-Printed Sensors Via an Histidine Tail. Application to the Detection of Pesticides Using Modified Cholinesterase," *Analytic Letters*, 34(4):529-540, (2001).

Armstrong, F.A., et al., "Recent Developments in Faradaic Bioelectrochemistry," *Electrochimica Acta*, 45:2623-2645, (2000).

Boireau, W. et al., "Bioengineering and Characterization of DNA-Protein Assemblies Floating on Supported Membranes," Biotechnology and Bioengineering, 77(2):225-231 (2002).

Bornscheuer, U., Angew. Chem. Int. Ed., 42:3336-3337 (2003).

Cabbiness, D.K., et al., "Macrocyclic Effect on the Stability of Copper(II) Tetramine Complexes", *J. Am. Chem. Soc.*, 91:6540-6541 (1969).

Chaga, G.S., et al., "Twenty-five years of immobilized metal ion affinity chromatography: past, present and future," *J. Biochem. Biophys, Methods*.

Chen, X., et al., "De Novo Design of a Cytochrome *b* Maquette for Electron Transfer and Coupled Reactions on Electrodes," *J. Phys. Chem. B*, 106:617-624 (2002).

Chi, Q., et al., "Ordered Assembly and Controlled Electron Transfer of the Blue Copper Protein Azurin at Gold (111) Single-Crystal Substrates," *J. Phys. Chem. B*. 105:4669-4679 (2001).

Clark, R., et al., "Voltammetric Peak Broadening for Cytochrome c/ Alkanethiolate Monolayer Structures: Dispersion of Formal Potentials," Alkanethiolate Monolayer Structures: Dispersion of Formal Potentials, *Langmuir*, 13:559-565 (1997).

Collinson, M., et al., "Voltammetry of Covalently Immobilized Cytochrome *c* on Self-Assembled Monolayer Electrodes," *Langmuir*, 8:1247-1250 (1992).

Comba, P., et al., "Fit and Misfit Between Ligands and Metal Ions," *Coordination Chemistry Reviews*, 238-239:21-29 (2003).

Cooper, J., "Direct Electron Transfer Reactions Between Immobilized Cytochrome *c* and Modified Gold Electrodes," *J. Electroanal. Chem.*, 347:267-275 (1993).

Cooper, M., "Optical Biosensors in Drug Discovery," *Nature Reviews*, 1:515-527 (2002).

Cosnier, S., "Biomolecule Immobilization on Electrode Surfaces by Entrapnment or Attachment to Electrochemically Polymerized Films," *Biosensors & Bioelectronics*, 14:443-456 (1999).

Courty, S. et al., "Two-Dimensional Crystallization of a Histidine-Tagged Protein on Monolayers of Fluidity-Enhanced $Ni^{2+}$-Chelating Lipids," *Langmuir*, 18:9502-9512 (2002).

Dabrowski, M., et al., "Strategies for Protein-Based Nanofabrication: $Ni^{2+}$ -NTA as a Chemical Mask to Control Biologically Imposed Symmetry," Chem. Biol., 5:689-697 (1998).

Das, K., et al., "Redox Systems of the Cell: Possible Links and Implications," *PNAS*, 99(15):9617-9618 (2002).

Dietrich, C., et al., "Functional Immobilization of a DNA-Binding Protein at a Membrane Interface Via Histidine Tag and Synthetic Chelator Lipids," *Biochemistry*.

Döbeli, H., et al., "Recombinant Fusion Proteins for the Industrial Production of Disulfide Bridge Containing Peptides: Purification, Oxidation without Concatamer Formation, and Selective Cleavage," *Protein Expression and Purification*, 12:404-414 (1998).

Dong, S., et al., "Some New Aspects in Biosensors," *Molecular Biotechnology*, 82:303-323 (2002).

Dorn, I., et al., "Molecular Recognition of Histidine-Tagged Molecules by Metal-Chelating Lipids Monitored by Fluorescence Energy Transfer and Correlation Spectroscopy," *J. Am. Chem. Soc.*, 120:2753-2763 (1998).

Einhauer, A., et al., "The FLAG™ Peptide, A Versatile Fusion Tag for the Purification of Recombinant Proteins," *J. Biochem. Biophys, Methods*, 49:455-465 (2001).

Ferapontova, E., et al., "P-Chip and P-Chip Bienzyme Electrodes Based on Recombinant Forms of Horseradish Peroxidase Immobilized on Gold Electrodes," *Biochemistry* (Mosc), 66:832-839 (2001).

Fivash, M., et al., "BIAcore for Macromolecular Interaction," *Curr. Opin. Biotechnol.*, 9:97-101 (1998).

Frey, B., et al., "Covalent Attachment and Derivatization of Poly(1-Lysine) Monolayers on Gold Surfaces as Characterized by Polarization—Modulation FT-IR Spectroscopy," *Anal. Chem.*, 68:3187-3193 (1996).

Geiβer, B., et al., "Selective Recognition of Copper(II) by a Water-Soluble, Emitter-Receptor Conjugate Containing a Ruthenium Chromophore, a Lysine Bridge, and a Cyclen Unit," *Eur. J. Inorg. Chem.*, 1543-1549 (2001).

Gershon, P. A., et al., "Stable Chelating Linkage for Reversible Immobilization of Oligohistidine Tagged Proteins in the BIAcore Surface Plasmon Res9onance Detector," *Journal of Immunological Methods*, 183:65-76 (1995).

Gilardi, G., et al., "Manipulating Redox Systems: Application to Nanotechnology," *Trends in Biotechnology*, 19:11:468-472 (2001).

Gilardi, G., et al., "Engineering and Design in the Bioelectrochemistry of Metalloproteins," *Curr. Opin. Biotechnol.* 9:97-101 (1998).

Glynou, Kyriaki et al., "One-step purification and refolding of recombinant photoprotein aequorin by immobilized metal-ion affinity chromatography", *Protein Expression & Purification* 27:384-390 (2003).

Gobi, K., et al., "Electrochemical Characteristics of Self-assembled Monoloayers of a Novel Nickel(ii) Pentaazamacrocyclic Complex on a Gold Electrode," *Langmuir*, 14:11008-1115 (1998).

Gooding, J. et al., Platinum-Catalyzed Enzyme Electrodes Immobilized on Gold Using Self-Assembled Layers, *Anal. Chem.* 70:2396-2402 (1998).

Gooding, J., et al., "Self-Assembled Monolayers into the $21^{st}$ Century: Recent Advances and Applications," *Electroanalysis*, 15(2):81-96 (2003).

Gorton, L., et al., "Direct Electron Transfer Between Heme-Containing Enzymes and Electrodes as Basis for Third Generation Biosensors," *Anal. Chim. Acta*, 400:91-108 (1999).

Green, R., et al., "Surface Plasmon Resonance Analysis of Dynamic Biological Interactions with Biomaterials," *Biomaterials*, 21:1823-1835 (2000).

Guengerich, F.P., "Cytochrome P450 Enzymes in the Generation of Commercial Products," *Nature Reviews*, 1:359-366 (2002).

Hainfield, J., et al., "Ni-NTA-Gold Clusters Target His-Tagged Proteins," *Journal of Structural Biology*, 127:185-198 (1999).

Hefti, Marco H. et al., "A His-tag based immobilization method for the preparation and reconstitution of apoflavoproteins", *Biochimica et Biophysica Acta* 1619:139-143 (2003).

Janknecht, R., et al., "Rapid and Efficient Purification of Native Histidine-Tagged Protein Expressed by Recombinant Vaccinia Virus," *Proc. Natl. Acad. Sci. USA*, 88:8972-8976 (1991).

Jiang, W. et al., "Protein Selectivity with Immobilized Metal Ion-tacn Sorbents: Chromatographic Studies with Human Serum Proteins and Several Other Globular Proteins", article No. AB972395 *Analytical Biochem.* 255:47-58 (1998).

Johnson, Colin P. et al., "Engineered Protein A for the Orientational Control of Immobilized Proteins", *Bioconjugate Chem.* 14:974-978 (2003).

Johnson, D.L. et al., "The influence of promoter and of electrode material on the cyclic voltammetry of *Pisum sativum* plastocyanin", Biolelectrochemistry 58:137-147 (2002).

Johnson, D.L. et al., "Electrochemical Characterization of Purified *Rhus vernicifera* Laccase: Voltammetric Evidence for a Sequential Four-Electron Transfer", *Biochemistry* 42:10229-10237 (2003).

Johnson, Daniel et al., "Electrochemical behavior of human adrenodoxin on a pyrolytic graphite electrode", *Bioelectrochemistry* 59:41-47 (2003).

Jones, Chris et al., "Current trends in molecular recognition and bioseparation", *Journal of Chromatography* 707:3-22 (1995).

Kapanidis, A.N. et al., "Site-Specific Incorporation of Fluorescent Probes into Protein: Hexahistidine-Tag-Mediated Fluorescent Labeling with $(Ni^{2+}:Nitrilotriacetic\ Acid)_n$—Fluorochrome Conjugates", *J. Am. Chem. Soc.* 123:12123-12125 (2001).

Kröger, Dietmar et al., "Immobilization of histidine-tagged proteins on gold surfaces using chelator thioalkanes", *Biosensors & Bioelectronics* 14:155-161 (1999).

Kumar A., et al., "Binding of Cu(II)-Poly (N-isopropylacrylamide/vinylimidazole) Copolymer to Histidine-Tagged Protein: a Surface Plasmon Resonance Study", *Langmuir* 19: 865-871 (2003).

Lauer, Sabine A. et al., "Development and Characterization of Ni-NTA-Bearing Microspheres", *Cytometry* 48:136-145 (2002).

Leonard, Paul et al., "Advances in biosensors for detection of pathogens in food and water", *Enzyme and Microbial Technology* 32:32-13 (2003.

Madoz-Gúrpide, Juan et al., "Modulation of Electroenzymatic NADPH Oxidation through Oriented Immobilization of Ferredoxin:$NADP^+$ Reductase onto Modified Gold Electrodes", *J. Am. Chem. Soc.* 122:9808-9817 (2000).

Mateo, Cesar et al. "One-Step Purification, Covalent Immobilization, and Additional Stabilization of Poly-His-Tagged Proteins Using Novel Heterofunctional Chelate-Epoxy Supports", *Biotechnology and Bioengineering* 76(3): 269-276 (2001).

Mössner, Ekkehard et al., "Importance of Redox Potential for the in Vivo Function of the Cytoplasmic Disulfide Reductant Thioredoxin from *Escherichia coli*", *The Journal of Biological Chemistry*, 274(36):252524-25259 (1999).

Murata, Masaharu et al., "Novel Biosensor for the Rapid Measurement of Estrogen Based on a Ligand-Receptor Interaction", *Analytical Sciences* 17:387-390 (2001).

Nieba, Lars et al., "BIACORE Analysis of Histidine-Tagged Proteins Using a Chelating NTA Sensor Chip", *Analytical Biochemistry* 252:217-228 (1997).

Nock, Steffen et al., "Reversible, site-specific immobilization of polyarginine-tagged fusion proteins on mica surfaces", *FEBS Letters* 414:233-238 (1997).

O'Shannessy, Daniel J. et al., "Detection and Quantitation of Hexa-Histidine-Tagged Recombinant Plasmon Resonance Biosensor Technique", *Analytical Biochemistry* 229:119-124 (1995).

Paborsky, Lisa et al., "A Nickel Chelate Microtiter Plate Assay for Six Histidine-Containing Proteins", *Analytical Biochemistry* 234:60-65 (1996).

Patel, Nikin et al., "Immobilization of Protein Molecules onto Homogeneous and Mixed Carboxylate-Terminated Self—Assembled Monolayers", *Langmuir* 13:6485-6490 (1997).

Porath, Jerker et al., "Metal chelate affinity chromatography, a new approach to protein fractionation", *Nature* 258:598-599 (1975).

Rädler, Ulf et al., "Design of Supported Membranes Tethered via Metal-Affinity Ligand-Receptor Pairs", *Biophysical Journal* 79:3144-3152 (2000).

Rowe, Gary K. et al., "Consequence s of Kinetic Dispersion on the Electrochemistry of an Adsorbed Redox-Active Monolayer", *Langmuir* 11:1797-1806 (1995).

Roy, Bidhan C. et al., "Synthesis of New Polymerizable Metal-Chelating Lipids", *J. Org. Chem.*, 64:2969-2974 (1999).

Schmitt, Lutz et al., "A Metal-Chelating Microscopy Tip as a New Toolbox for Single-Molecule Experiments by Atomic Force Microscopy", *Biophysical Journal* 7:3275-3285 (2000).

Shumyantseva, Victoria V. et al., "Construction and characterization of bioelectrocatalytic sensors based on cytochromes P450", *Journal of Inorganic Biochemistry* 87:184-190 (2001).

Sigal, George B. et al., "A Self-Assembled Monolayer for the Binding and Study of Histidine-Tagged Proteins by Surface Plasmon Resonance", *Anal. Chem.* 68:490-497 (1996).

Song, Shihua et al., "Characterization of Cytochrome c/Alkanethiolate Structures Prepared by Self-Assembly on Gold", *J. Phys. Chem.* 97:6564-6572 (1993).

Stora, T. et al., "Metal Ion Trace Detection by a Chelator-Modified Gold Electrode: A Comparison of Surface to Bulk Affinity", *Langmuir* 13(20):5211-5214 (1997).

Terpe K., "Overview of tag protein fusions: from molecular and biochemical fundamentals to commercial systems", *Appl. Microbiol. Biotechnol.* 60:523-533 (2003).

Thess, Andreas et al., "Specific Orientation and Two-dimensional Crystallization of the Proteasome at Metal-chelating Lipid Interfaces", *The Journal of Biological Chemistry* 277(39):36321-36328.

Ulman, Abraham, "Formation and Structure of Self-Assembled Monolayers", *Chem. Rev.* 96:1533-1554 (1996).

Veiseh, Mandana et al., "Highly Selective Protein Patterning on Gold-Silicon Substrates for Biosensor Applications", *Langmuir* 18:6671-6678 (2002).

Volkov, Alexander et al., "Evidence for Intramolecular Processing of Prosubtilisin Sequestered on a Solid Support", *J. Mol. Bio.* 262:595-599 (1996).

Wang, Chung-Yih et al., "Specific Immobilization of Firefly Luciferase through a Biotin Carboxyl Carrier Protein Domain", *Analytical Biochemistry* 246:133-139 (1997).

Warden, Andrew et al., "Synthesis of Novel Derivatives of 1,4,7-Triazacyclononane", *Organic Letters* 3(18):2855-2858 (2001).

Weisman, Gary R. et al., "Selective N-Protection of Medium-ring Triamines", *J. Chem. Soc., Chem. Commun.*, pp. 886-887 (1987).

Wojtyk, James T. C. et al., "Modification of Porous Silicon Surfaces with Activated Ester Monolayers", *Langmuir* 18:6081-6087 (2002).

Xiao, Yi et al., "'Plugging into Enzymes': Nanowiring or Redox Enzymes by a Gold Nanoparticle", *Science* 299:1877-1881 (2003).

Zachariou, Michael et al., "Application of Immobilized Metal Ion Chelate Complexes as Pseudocation Exchange Adsorbents for Protein Separation", *Biochemistry* 35:202-211 (1996).

Zachariou, Michael et al., "Adsorption and selectivity characteristics of several human serum proteins with immobilized hard Lewis metal ion—chelate adsorbents", *Journal of Chromatography* 890:95-116 (2000).

Zachariou, Michael et al., "Potentiometric Investigations into the Acid-Base and Metal Ion Binding Properties of Immobilized Metal Ion Affinity Chromatographic (IMAC) Adsorbents", *J. Phys. Chem.* 100:12680-12690 (1996).

Zachariou, Michael et al., Characterization by Potentiometric Procedures of the Acid—Base and Metal Binding Properties of Two New Classes of Immobilized Metal Ion Affinity Adsorbents Developed for Protein Purification, *Anal. Chem.* 69:813-822 (1997).

Zhang, Juan Kun et al., "A Study of His-Tagged Alkaline Phosphatase Immobilization on a Nanoporous Nickel-Titanium Dioxide Film", *Analytical Biochemistry* 292:307-310 (2001).

Zhang, Zhe et al., "Direct electron injection form electrodes to cytochrome $P450_{cam}$ in biomembrane-like films", *J. Chem. Soc.* 93(9):1769-1774, Faraday Trans. (1997).

International Search Report issued for PCT/AU2004/000923 on Aug. 31, 2004.

Sensor Chip CM5 [online]. Biacore Life Sciences, [retrieved on Feb. 13, 2009]. Retrieved from the Internet: <URL: http://www.biacore.com/lifesciences/products/sensor_chips/cm5.index.html>.

Wainright, Kevin P., "Synthetic and structural aspects of the chemistry of saturated polyaza macrocyclic ligands bearing pendant coordinating groups attached to nitrogen", *Coordination Chemistry Reviews*, 1997, vol. 166, pp. 35-90.

Du Roure, O., et al., "Functionalizing Surfaces with Nickel Ions for the Grafting of Proteins", *Langmuir*, 2003, vol. 19, pp. 4138-4143.

Supplementary European Search Report, dated Aug. 26, 2009, issued in EP Application No. EP 04 73 7544.

* cited by examiner

SENSOR CHIPS

PRIORITY CLAIM

This application is a continuation-in-part of International Application PCT/AU2004/000923 having an international filing date of Jul. 8, 2004, which itself claims the benefit of priority to Australian application 2003903504, filed Jul. 8, 2003, both of which are incorporated herein by reference in their entirety.

FIELD OF THE INVENTION

The present invention relates to sensor chips of the type that have a monolayer of molecules immobilised on a substrate surface. The sensor chips may be used to investigate interactions between the immobilised molecules and other molecules or to investigate interactions between the immobilised molecules and the substrate surface.

BACKGROUND OF THE INVENTION

The investigation and/or analysis of ligand-molecule interactions and/or the electrochemical behaviour of biomolecules are fundamentally important in many fields, including biology, immunology, chemistry and pharmacology.

A number of analytical techniques can be used to investigate ligand-molecule interactions. For example, biological analytes can be detected or quantified based on ligand-specific binding between a ligand and a receptor. Common ligand/receptor binding pairs include antigen-antibody, hormone-receptor, drug-receptor, cell surface antigen-lectin, biotin-avidin, substrate-enzyme, and complementary nucleic acid strands. The analyte to be detected may be either member of the binding pair; alternatively, the analyte may be a ligand analogue that competes with the ligand for binding to the receptor.

Other analytical techniques utilise the oxidation or reduction of a molecule on the surface of a solid support. For example, glucose sensors may include an enzyme, such as glucose oxidase, which converts glucose into reaction products including hydrogen peroxide. A suitable electrode can then measure the formation of hydrogen peroxide as an electrical signal. The signal is produced following the transfer of electrons from the peroxide to the electrode, and under suitable conditions the enzyme catalysed flow of current is proportional to the glucose concentration in a sample. Alternatively, an electrode surface may be used in combination with current or impedance measuring elements for detecting a change in current or impedance in response to the presence of a ligand-receptor binding event.

Many of the aforementioned analytical techniques involve immobilising a molecule on a solid support. Other than immobilising the molecules, the solid support may play no role in subsequent chemical or biological investigations of the immobilised molecules. Alternatively, the solid support may interact with the immobilised molecule, such as when the solid support is an electrode which is used to investigate the electrochemistry of the molecule.

A common technique for the immobilization of molecules on the surface of a solid support is to covalently attach molecules onto a surface of a solid support that has previously been modified with an alkanethiol. Covalent attachment of the molecules to the surface prohibits diffusion of the molecules away from the solid support and also typically results in the formation of a film of molecules that is limited to a single monolayer, thereby limiting the required sample volume. The formation of self-assembled monolayers ("SAMs") of molecules in this way has enabled the design of new interfaces for the study of ligand-molecule binding interactions as well as specific redox-active analytes. For example, monolayers have been formed via alkanethiol-gold linkage and related linkages between carboxylates and phosphonates and metal oxide surfaces. Monolayers formed on gold surfaces are particularly suited for studying biomolecular recognition at surfaces because the well-defined structures are amenable to detailed characterization at a molecular level by using, for example, scanning tunneling microscopy, atomic force microscopy as well as other optical and electrochemical bioanalytical techniques.

Solid supports having a monolayer of immobilised molecules are commonly referred to as "chips" or "sensor chips". The sensor chips are routinely used in biosensor instruments where one or more properties of the immobilised molecules may be measured. A representative class of biosensor instrumentation is sold by Biacore AB (Uppsala, Sweden) under the trade name BIAcore™ (hereinafter referred to as "the BIAcore instrument"). The BIAcore instrument includes a light emitting diode, a sensor chip covered with a thin gold film, an integrated fluid cartridge and a photodetector. Molecules that are receptors of an analyte of interest are immobilised on the surface of the sensor chip and the chip is contacted with a flow of sample containing the analyte of interest. Any change in the surface optical characteristics of the sensor chip arising from the binding of the analyte of interest are then measured by detecting any intensity loss or "dip" in light that is reflected from the gold film on the surface of the sensor chip.

Numerous devices for determination of analytes that are based on the use of sensor chips are now available. However, many of the available sensor chips have some limitation with respect to sensitivity, test sample volume, reproducibility, speed of response, number of effective uses, or the range of detection. In the clinical setting, it is a goal to maximize the data obtainable from relatively small test sample volumes during analysis of fluids.

The discussion of the background to the invention herein is included to explain the context of the invention. This is not to be taken as an admission that any of the material referred to was published, known or part of the common general knowledge in any country. Further, throughout this specification reference may be made to documents for the purpose of describing various aspects of the invention. However, no admission is made that any document cited in this specification forms part of the common general knowledge in the art in any country.

SUMMARY OF THE INVENTION

The present invention arises out of studies conducted by the inventors that have shown that by uniformly orienting molecules on the surface of a solid substrate so that the active site is uniformly orientated on the surface it is possible to increase the efficiency of any interaction of the immobilized molecule with a solution phase or with the solid support. If the active sites or recognition domains of every immobilized molecule are facing an appropriate solution phase, then each molecule is capable of interacting with an appropriate substrate and contributing to the overall biosensor response. An optimized detection layer can be expected to display increased sensitivity and reliability, potentially enhancing the range of suitable applications and reducing manufacturing costs.

The present invention provides a method for selectively orienting and immobilizing molecules on a surface of a solid support, the method comprising:
attaching a linker molecule to the surface of the solid support, the linker molecule including a head group that is capable of binding to the solid support, and a tail group that is capable of chelating to a metal ion;
treating the solid support with a solution containing the metal ion so that the metal ion is chelated to the tail group;
attaching a metal ion chelating tag to the molecules to form tagged molecules; and
capturing the tagged molecules on the solid support by contacting it with the tagged molecules to form a monolayer of molecules on the surface of the solid support in which a majority of the molecules are held in the same orientation with respect to the surface.

The present invention also provides a sensor chip including a monolayer of immobilised molecules captured on a surface of a solid support, wherein a majority of the immobilised molecules are in the same orientation with respect to the surface.

The present invention also provides a sensor chip including:
a linker molecule attached to the surface of a solid support, the linker molecule including a head group that is bound to the solid support, and a tail group that is chelated to a metal ion;
a monolayer of molecules on the surface of the solid support, wherein each molecule contains a metal ion chelating tag and is held on the surface of the solid support by co-ordination of the tag with the metal ion such that a majority of the molecules are held in the same orientation with respect to the surface.

To determine whether or not "a majority of the molecules are held in the same orientation with respect to the surface" it is possible to compare the redox response for molecules oriented on a solid support using the method of the present invention and measuring the electrochemical response over increasing scan rates. The molecules are taken to be oriented if an improved electrochemical reversibility is observed.

Preferably, the tail group of the linker molecule is a cyclic ligand containing three or more atoms that are capable of coordinating to the metal ion. More preferably, the tail group is a tetradentate macrocycle that is capable of chelating with the metal ion.

The present invention further provides a method for selectively orienting and immobilizing molecules on a surface of a solid support, the method including the steps of:
attaching a linker molecule to a gold surface on the solid support, the linker molecule including a head group that is capable of binding to the gold surface, a tetradentate macrocycle tail group that is capable of chelating to a metal ion and a spacer extending between the head group and the tail group;
contacting the solid support with a solution containing the metal ion so that the metal ion is coordinated with the macrocycle;
attaching a tag that is capable of coordinating with the metal to the molecules to form tagged molecules; and
capturing the tagged molecules on the solid support by contacting it with the tagged molecules such that the tag is coordinated with the metal ion to form a monolayer of molecules on the surface of the solid support in which a majority of the molecules are held in the same orientation with respect to the surface.

As a result of the macrocyclic effect, the use of a macrocycle tail group may provide for tighter binding of the metal ion to thereby reduce leakage of metal ions from the support. This ultimately leads to a reduction in "metal bleeding" from the biosensor. The term "macrocyclic effect" refers to the greater thermodynamic stability of a complex with a cyclic polydentate ligand when compared to the complex formed by a comparable non-cyclic ligand.

The present invention also provides a biosensor device including:
a sensor chip of the present invention; and
a transducer for detecting a change in a parameter in the immobilized molecules on the sensor chip.

The present invention also provides a method for increasing the sensitivity of measurement of a parameter of a molecule that is immobilized on a solid support, the method including the step of orienting the molecule on the solid support using the method described herein.

The present invention also provides a method for increasing the reproducibility and/or sensitivity of measurement of an electrochemical parameter of a redox active molecule that is immobilized on a solid support electrode, the method including the steps of:
attaching a linker molecule to a surface on the solid support electrode, the linker molecule including a head group that is capable of binding to the solid support, a tail group that is capable of chelating to a metal ion, and an alkyl chain of more than two atoms in length between the head group and the tail group;
treating the solid support with a solution containing the metal ion so that the metal ion is chelated to the tail group;
attaching a metal ion chelating tag to the redox active molecules to form tagged molecules; and
capturing the tagged redox active molecules on the solid support by contacting it with the tagged molecules to form an immobilised monolayer of redox active molecules on the surface of the solid support in which a majority of the molecules are held in the same orientation with respect to the surface.

The present invention also provides a method of determining the presence of an analyte in a sample, the method including the steps of:
providing a self-assembled monolayer on a surface of a solid support, said monolayer comprising linker molecules having head groups that are bound to the a surface of the solid support, and tail groups that are chelated to a metal ion; and analyte binding molecules having a tag that is bound to the metal ion, said analyte binding molecules oriented uniformly with respect to the surface of the solid support;
contacting the self-assembled monolayer having the analyte binding molecule immobilised thereon with a sample suspected of containing a target analyte; and
detecting binding of the target analyte with the analyte binding molecule to thereby determine the presence or absence of the target analyte.

BRIEF DESCRIPTION OF THE FIGURES

FIG. 2 shows a plot of wavenumber vs absorbance for a Diffuse Reflectance Infrared Fourier Transform (DRIFT)

spectroscopy study on the surface chemistry of SAMs that were formed according to the methods of the present invention.

DESCRIPTION OF THE INVENTION

Before proceeding with a description of the present invention, some of the terms that will be used throughout this specification will now be defined.

The term "molecule" as used throughout the specification is to be understood to mean any carbon-based molecule for which a chemical and/or physical parameters or characteristics can be measured or determined by capturing the molecule on a solid support surface. The molecule could be any protein, peptide, nucleic acid, carbohydrate, lipid or synthetic molecule.

The term "orientation" when used in the specification in relation to the placement of a molecule with respect to the surface of a solid support is to be understood to mean the position and attitude of the molecule with respect to the solid support surface.

The term "immobilized" when used in the specification in relation to molecules on the surface of a solid support is to be understood to mean that the molecules are bound to the solid support under conditions in which the solid support is intended to be used.

Under such conditions, the molecules are not able to migrate from the surface of the solid support. However, it is to be understood that the molecules may be reversibly bound so that they can be removed from the solid support under specific conditions.

The term "biosensor" when used in the specification is to be understood to mean a system, substrate or device that detects a chemical or biological species with high selectivity on the basis of molecular recognition. A biosensor uses a biological element, such as an immobilized peptide, protein, poly- or oligonucleotide or cell, as a sensor. A biosensor may use specific biochemical reactions to detect molecules by electrical, thermal or optical signals. Alternatively, a biosensor may be in the form of a solid support having a layer of immobilised biological elements for use in immunoassays, including, but not limited to, solid phase enzyme-linked immunosorbent assays, radioimmunoassays, fluoroimmunoassays etc.

As previously discussed, the present invention provides a method for immobilizing and selectively orienting molecules on a surface of a solid support. The method includes the steps of:

attaching a linker molecule to the surface of the solid support, the linker molecule including a head group that is capable of binding to the solid support, and a tail group that is capable of chelating to a metal ion;

treating the solid support with a solution containing the metal ion so that the metal ion is chelated to the tail group;

attaching a metal ion chelating tag to the molecules to form tagged molecules; and capturing the tagged molecules on the solid support by contacting it with the tagged molecules to form a monolayer of molecules on the surface of the solid support in which a majority of the molecules are held in the same orientation with respect to the surface.

By selectively orienting the molecules on the surface of the solid support it may be possible to increase the sensitivity of an analytical determination that is being made when compared to existing methods because most of the molecules are oriented with an active site in a position suitable for reaction. In the case of proteins, using existing methods control over protein orientation is limited, since any surface amines can provide a point of attachment of the protein to the linker molecule. Consequently, two adjacent protein molecules may well be up to 180° with respect to each other, since the monolayer forms by random coupling events. In order to analyze for a specific substrate, specific region(s) on the protein surface must be available to optimize sensor performance. Under the random coupling scenario, as much as half of the protein monolayer may be in an orientation unsuitable for substrate conversion.

The tag in the tagged molecule is preferably covalently bound to the molecule at a position on the molecule that is separated from the active site (or recognition region) of the molecule. It will be appreciated that the active site of the molecule is that portion of the molecule that is involved in the chemical and/or physical transformation that is being investigated whist the molecule is captured on the solid support. For example, in the case of a polypeptide or protein, the tag may be covalently bound anywhere on the protein, as long as the protein activity is not affected. In this way the protein is attached to the solid support at a modified portion of the protein and not a native portion of the protein. In the case of a small organic molecule the tag may be attached to the small organic molecule via a flexible linker chain that acts to separate the tag from the active site of the molecule. The linker chain may be a functionalized alkyl chain, for example.

The tag is preferably a small peptide chain containing chelate forming amino acids. Suitable chelate forming amino acids include cysteine, lysine, histidine, arginine. More preferably, the tag is a peptide containing a minimum of two but preferably four to six histidine residues. Preferably, the peptide chain contains a histidine rich domain. The tag may contain three histidine residues and three other amino acid residues that assist with removal of the tag from the molecule. Most preferably the tag is a peptide containing six consecutive histidine residues herein referred to as a "6*his" tag. The 6*his tag has been found to be particularly suitable for binding to a chelating metal ion.

The solid support onto which the linker molecule is attached may be in any suitable form, such as foils, wires, wafers, chips, micro- or nano-particles, semiconductor devices and coatings deposited by any known deposition process. The solid support material may be a metal, metal oxide, silica, glass, quartz, plastic, or polymer surface (modified or unmodified). Suitable polymer surfaces include dextran, polycarbonate etc.

In one preferred form of the invention the solid support onto which the linker molecule is attached is a noble metal. Suitable noble metals include silver, gold, platinum and palladium. In addition, graphite-based materials, $TiO_2$, $IrO_2$, $SnO_2$, Si-based surfaces or clays may also be used as a solid support. The solid support may be a chip having a surface that is formed from one of the aforementioned materials. The chip itself may be formed from any suitable material including but not limited to glass, plastic or ceramic material. Most preferably, the solid support includes a gold surface.

The solid support may also be a chromatography medium, such as dextran, silica etc, and derivatives thereof. In this form, the present invention may be used for binding and separation of biomolecules, such as peptides and proteins. Thus, the present invention may be used in immobilized metal affinity chromatography.

The linker molecule may be attached to the solid support either directly or indirectly. For example, the head of the linker molecule may be bonded to a noble metal surface on the solid support. Alternatively, the solid support may have a coating, such as a dextran coating, onto which the linker molecule is attached.

The linker molecule comprises the head group, the tail group, and a spacer group between the head group and tail group. The spacer group is covalently attached to the head and tail groups, and one function of the spacer group is to locate the tail group away from the surface of the solid support. Preferably the spacer is a carbon-based chain between the head and tail groups. Preferably, the carbon-based chain is an alkyl chain or an alkyl chain containing heteroatoms such as O, N, Si, P, or S. For example, the carbon based chain may be a —$(CH_2)_n$— group, where n is an integer from 1 to 50, more preferably 2 to 15, and even more preferably 3 to 10. Alternatively, the carbon based chain may include a heteroatom and, for example, may be a —$(CH_2CH_2O)_n$— group, where n is an integer from 1 to 50, more preferably 3 to 10. The length of the carbon-based chain can be chosen depending on the application envisaged, and may be from 1 to 50 atoms in length. In one preferred form of the invention the carbon based chain is two to six atoms in length and most preferably three atoms in length between the tail group and the head group. However, depending on the use of the sensor, the linker may be up to 50 atoms in length.

Preferably, the head group is a heteroatom that has a relatively high affinity for the noble metal surface or other surface to which it is to be attached. Sulfur and selenium are particularly preferred head groups for noble metal substrates, whilst oxygen is preferred for silica solid support substrates. However, any atom (e.g., Si) or group that can react with the surfaces listed above may be used.

In a particularly preferred form of the invention the tail group is a cyclic ligand containing three or more atoms that are capable or coordinating to the metal ion. Multidentate macrocycles containing three or more heterodonor atoms including O, S, Se, N, P, As or any atom that can act as a Lewis base are particularly preferred. Multidentate macrocycles may have greater than three heterodonor atoms, and more preferably 3 to 15 heterodonor atoms. In a preferred form of the invention, the multidentate macrocycle is a tetradentate macrocycle. The macrocycle is preferably a derivative of 1,4,7-triazacyclononane. More preferably, the derivative of 1,4,7-triazacyclononane contains a heterodonor atom that is pendant from the triazacyclononane ring. For example, the heterodonor atom may be the oxygen atom of a carbonyl group (ester, carboxylic acid, ketone, aldehyde, amide etc.). Most preferably the macrocycle is 1-acetato-4-benzyl-1,4,7-triazacyclononane.

The derivative of 1,4,7-triazacyclononane may contain an R group at the 4 position. The R group may be any suitable substituted or non-substituted alkyl or aryl group. In one preferred form of the invention, the R group is a benzyl group. The R group could also be any one of the nitrogen protecting or terminal groups that are known in the art. Examples of nitrogen protecting or terminal groups can be found in Greene and Wuts, *Protective Groups in Organic Synthesis,* 2nd ed, John Wiley & Sons, New York, 1991, the disclosure of which is hereby incorporated by reference in its entirety.

The metal ion can be any ion that is capable of chelating with heteroatoms such as N, S, O and the like. Preferably, the metal ion is capable of octahedral coordination. Suitable metal ions include zinc, copper, cobalt and nickel. Other metal ions that can be used include the alkali and alkaline earth metals, particularly sodium, potassium, magnesium, calcium and lithium.

In one preferred form of the invention the solid support is an electrode. In this way the solid support can form part of an electrochemical array so that the redox activity of the molecules immobilized on the surface can be determined. More specifically, the method of the present invention may be particularly suitable for direct electrochemical measurements of redox active proteins, such as thioredoxin and other proteins having a redox active site, including metalloproteins, or those containing organic cofactors. In this way it is possible to measure directly the redox 'signature' of a protein of interest. In a preferred form of the present invention the linker molecule is three atoms in length and thus the bound protein is held relatively close to the electrode. Close proximity to the electrode is associated with strong and reproducible signals for electrode sensors.

Alternatively, the solid support may form part of a chip, the surface of which is formed from a suitable material according to the present invention, for example a noble metal surface. The chip may be formed from glass, plastic, ceramic or the like. In this case, the immobilized molecules may be used to capture a specific analyte in a sample suspected of containing the analyte.

In particularly preferred embodiments of the present invention, the method involves: (i) the formation of a self assembled monolayer of mercaptopropionic acid ("MPA") on gold; (ii) the activation of the carboxylic acid groups to reaction with a nitrogen nucleophile; (iii) treatment of the activated substrate with a suitable derivative of 1,4,7-triazacyclononane; (iv) treatment of the subsequent reaction product with a solution containing the chelating metal ion $Zn^{2+}$; and (v) formation of a self assembled monolayer of protein (or other) molecules by treating the product from (iv) with 6*his tagged molecules.

Advantageously, the sensor chip of the present invention can be regenerated to bind the same or different molecules by washing the surface of the solid support with imadazole, acidic pH or addition of any ligand which is a Lewis base. In addition, the metal ion can be changed using EDTA or another known metal chelating ligands.

The present invention also provides a biosensor device including a sensor chip as hereinbefore described. The biosensor also includes a transducer for detecting a change in a parameter in the immobilised molecules on the sensor chip. The transducer may measure an electrical parameter, such as in a glucose biosensor, an optical parameter, such as in a Biacore instrument, or any other suitable parameter.

The skilled person will appreciate that the sensor chip of the present invention may be used in existing apparatus for measuring one or more parameters of the molecules immobilized on the surface of the sensor chip and/or molecules that bind to the molecules immobilized on the surface of the sensor chip. The apparatus typically includes a reaction substrate and a separate reader or detector device, such as a scintillation counter or spectrophotometer. Assays based on surface plasmon resonance (SPR) effects, such as the BIAcore™ instrument and methodology, may be used. These assays exploit the shift in SPR surface reflection angle that occurs with perturbations, e.g., binding events, at the SPR gold-glass interface. Applications include direct electrochemistry, including bioelectrochemistry, fluorescence or luminescence studies between interacting species or functional groups, and applications involving immunological interactions, such as antibody-antigen interactions.

It will also be appreciated that included within the scope of the present invention is the use of the layer of molecules held in the same orientation with respect to the surface for applications that do not involve measuring a parameter of molecules immobilized on the surface, but rather use the uniform orientation of the immobilized molecules as a scaffold. In this case, the uniform orientation of the immobilized molecules may be used as a scaffold, for example, for other molecules, molecular complexes, or cells.

Accordingly, in another form the present invention provides a solid support including a monolayer of immobilized molecules captured on the surface of the solid support, wherein a majority of the immobilized molecules are in the same orientation with respect to the surface, and further including one or more molecules attached or captured by the immobilized molecules on the surface of the solid support.

In addition, the methods of selectively orienting and immobilizing molecules on the surface of a solid support may include a further step of attaching or capturing one or more secondary molecules to the tagged molecules.

It will also be appreciated that included within the scope of the present invention is the use of the layer of molecules held in the same orientation with respect to the surface for applications in which the properties of the immobilized molecules are assessed without interaction with an analyte. For example, direct electrochemistry provides the ability to measure properties of a protein by electron exchange.

Accordingly, the present invention also provides a sensor device for measuring a parameter of an immobilized molecule on the surface of the sensor device.

Therefore, the present invention also provides a sensor device including a sensor chip of the present invention and a transducer for measuring a parameter in the immobilized molecules on the sensor chip.

REPRESENTATIVE EMBODIMENTS OF THE INVENTION

Representative embodiments of the invention will now be described by way of the following non-limiting examples.

Example 1

Preparation of Self Assembled Monolayers (SAMs)

Self assembled monolayers of molecules of interest were formed on a gold surface. The immobilization protocol is outlined in FIG. 1.

Figure 1:
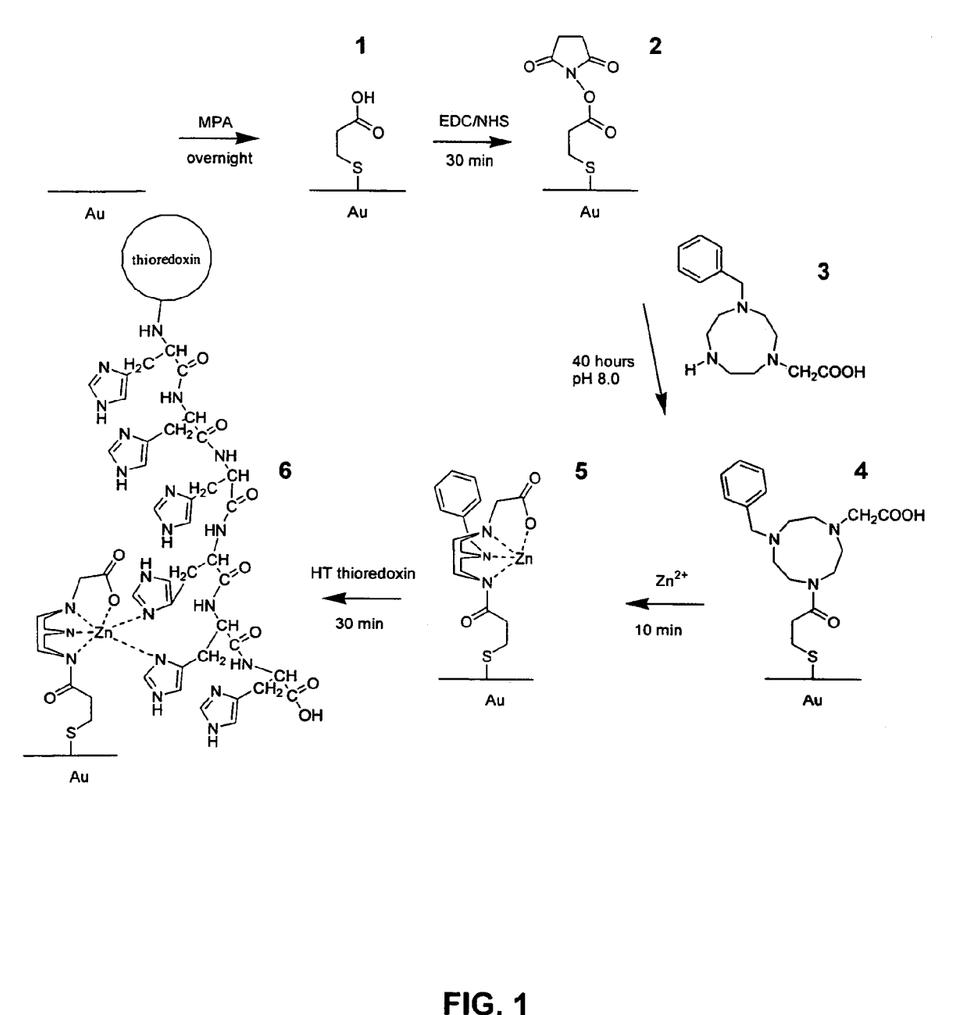
FIG. 1 is a schematic flow diagram showing a procedure for producing SAMs according to the methods of the present invention.

A clean gold surface was modified with a mercaptopropionic acid (MPA) SAM, designated 1 and the monolayer was subsequently modified with EDC/NHS to create the NHS intermediate 2. Specifically, a gold sheet was placed in a 5 mM solution of MPA (75:25 w/w Ethanol:$H_2O$) overnight. The surface was then washed with ethanol to remove unbound MPA, and dried under a stream of $N_2$. The dried gold sheet was placed into an aqueous solution containing 75 mM EDC and 25 mM NHS for 30 minutes, washed with water and used immediately.

The modified macrocyclic amine, 1-acetato-4 benzyl-1,4,7 triazacyclononane 3, was synthesized according to the method described in Warden et al. (*Org. Lett.* (2001) 3(18) 2855-2858) incorporated herein by reference. The gold sheet that had been modified to 2 was then placed into an aqueous solution containing 20 nM 1-acetato-4-benzyl-1,4,7-triazacyclononane 3 for 3 days. The pH of the solution was kept at $\geq 10$. The gold was then washed exhaustively with water and used immediately.

Addition of a metal desirous of octahedral coordination (pictured is $Zn^{2+}$) gives the coordination sites 5. Specifically, the gold sheet that had been modified to 4 was placed into a 20 mM solution of $ZnCl_2$ for 20 minutes. The gold was washed thoroughly with water, and then immersed in a dilute solution containing 6*his tagged molecules to afford the highly orientated protein monolayer 6. For example, the modified gold surface may be placed in an aqueous solution containing 6*his tagged thioredoxin (0.2 mg of protein/mL in 10 mM phosphate buffer, pH 6.0) at 4° C. overnight, washed in 10 mM phosphate buffer, pH 6.0 and used immediately.

Example 2

Analysis of SAMs

The SAMs prepared according to Example 1 were examined using electrochemical cell and surface characterization techniques that are described in the literature (see, e.g., D. L. Johnson, J. Thompson, S. M. Brinkmann, K. L. Schuller & L. L. Martin, "Electrochemical Characterisation of purified *Rhus vernicifera* laccase—voltametric evidence for a sequential 4-electron transfer," *Biochemistry* (2003), 42:10229-10237 and references therein).

Figure 2:
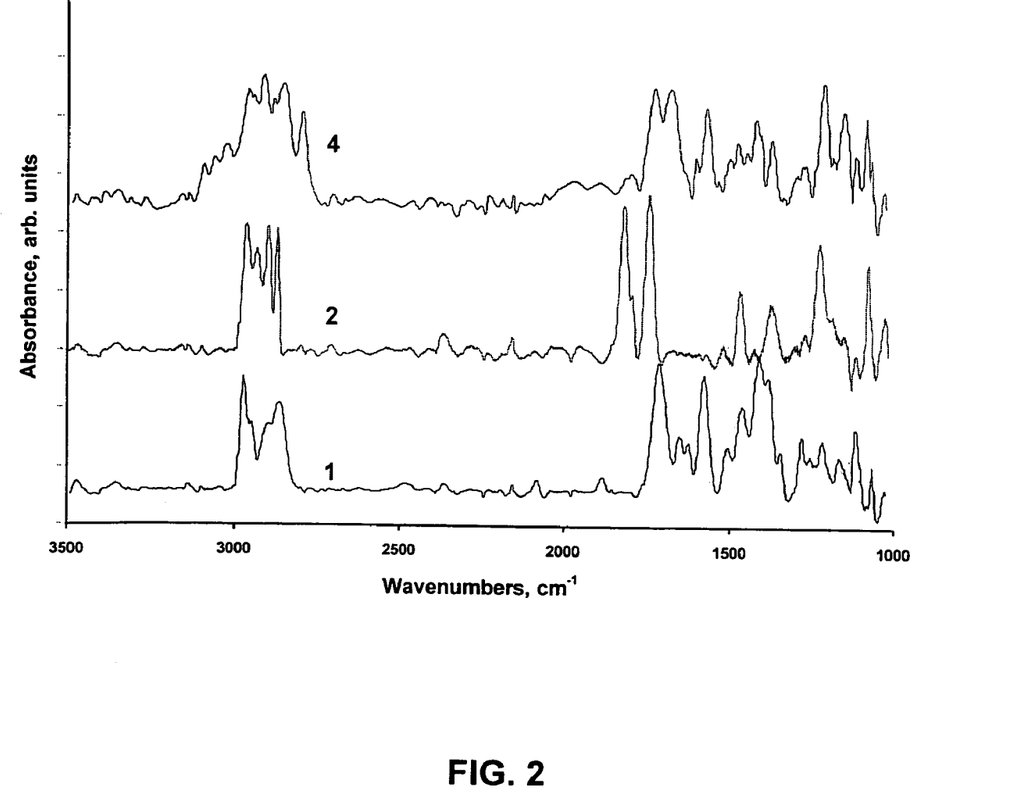

DRIFT (FIG. 2) and XPS experiments (not shown) were consistent with the proposed surface chemistry. DRIFT analysis was performed on fine silver powder modified according to FIG. 1. DRIFT analysis of the preparatory stages 1, 2, and 4 are shown in FIG. 2. Successful surface modification can be clearly seen in the C—H and C═O stretching regions. Structure 1 displays one C═O stretching vibration resulting from the COOH functionality, Structure 2 displays two distinct C═O stretching vibrations resulting from the —COON— moiety and from the carbonyl groups on the succinimide, and Structure 4 displays two different C═O stretching vibrations from the amide and from the COOH group on the macrocyclic amine. XPS measurements concur, with significant variation in the $N_{1s}$ and $O_{1s}$ binding regions.

Example 3

Electrochemical Behaviour of Immobilised Thioredoxin: Comparison of Oriented and Non-Oriented Monolayers The self assembled monolayer was studied using direct electrochemistry on histidine-tagged *E. coli* thioredoxin. Thioredoxin is the simplest member of a growing superfamily which regulate redox operation through a disulfide bond(s). The highly conserved active site contains two cysteine residues with the sequence Cys-XXX-XXX-Cys where X is any amino acid. The oxidized form contains a disulfide bond, and the reduced form, generated by the sequential addition of two electrons, contains two thiol groups.

The thioredoxin used in this study was expressed in *E. coli* using the Novagen expression plasmid vector pET-32a(+) containing the coding region of *E. coli* thioredoxin gene and six codons for additional histidine residues at the C terminus. The histidine-tagged thioredoxin was then purified to homogeneity as assessed by a single band on SDS-PAGE using a nickel affinity (Ni/NTA) column (QIAGEN). The sample was concentrated to 5 mg/mL and stored in potassium phosphate buffer (pH 7.4) at −80° C. before use.

Macrocycle modified electrodes were prepared by placing a gold electrode in a 5 mM solution of mercaptopropionic acid (MPA) (75:25 v/v ethanol/water) overnight. The electrode surface was then washed with ethanol to remove unbound MPA, and dried under a stream of nitrogen gas. The dried gold electrode was placed into an aqueous solution containing 75 mM 1-ethyl-3-(3-dimethylaminopropyl)carbodiimide (EDC) and 25 mM N-hydroxysuccinimide (NHS) for 30 minutes, washed with water and used immediately. The SAM-modified electrode was placed into an aqueous solution containing 20 mM 1-acetato-4-benzyl-1,4,7-triazacyclononane at pH 8 for ~30 h. The gold electrode was then washed with water and used immediately. Metal ions were incorporated into the macrocycle by placing the modified electrode into a 20 mM solution of $ZnCl_2$ for 20 minutes. The electrode was washed thoroughly with water, placed into an aqueous solution of thioredoxin (0.2 mg of histidine tagged thioredoxin/mL in 10 mM phosphate buffer, pH 7.4) at 4° C. for between 30 min and 3 h, then washed in the same buffer and used immediately. Alternatively, His-tagged cytochrome P450c17 and plastocyanin were immobilised overnight at 4° C. using a 20 mM protein solution in 10 mM phosphate buffer, pH 7.4. Covalent attachment of the thioredoxin directly to the electrode for comparison was done following the same procedure but without addition of the macrocyclic moiety, thereby resulting in its attachment to a surface amine on the thioredoxin protein.

All electrochemical measurements were obtained using a BAS 100B electrochemical analyser (Bioanalytical Systems Inc., Lafayette, USA) at room temperature. A conventional electrochemical set-up was employed, involving an Ag/AgCl (3 M KCl) reference electrode, a platinum auxiliary electrode and a gold electrode either in the form of a button electrode (from BAS) or a gold sheet. Potentials were corrected to the normal hydrogen electrode (NHE).

Figure 3:
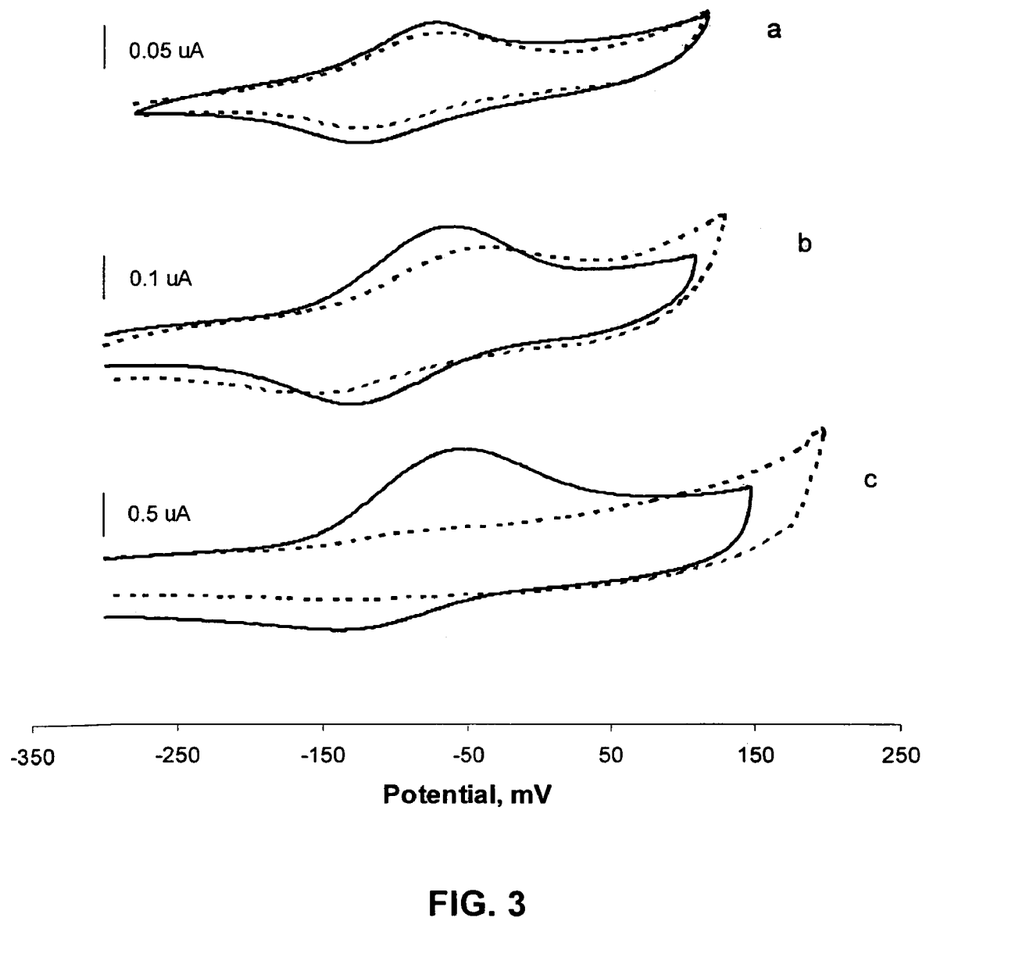
FIG. 3 shows typical cyclic voltammograms of histidine tagged thioredoxin obtained at a AcBztacn modified gold electrode (5, solid line) compared with those obtained when the protein is covalently bound to the electrode via surface lysine residues at stage 2 (dashed line). The one-electron reduction of the oxidised thioredoxin to the radical anion is shown. Scan rates are (a) 0.2 mV/s (b) 1.0 mV/s and (c) 10 mV/s. Current responses are indicated for each scan rate in 20 mM phosphate buffer (pH 7.4).
Figure 4:
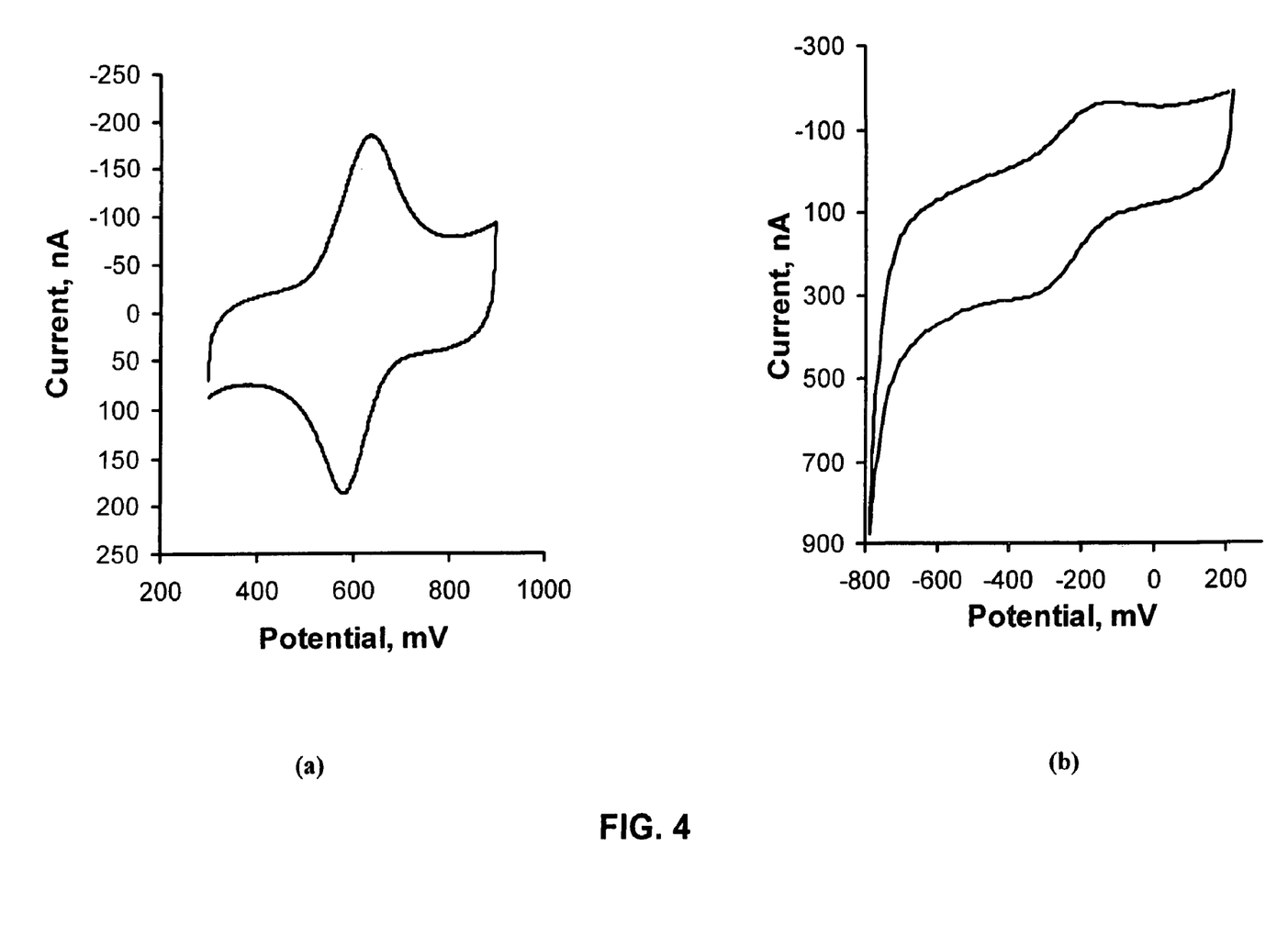
FIG. 4 shows a cyclic voltammogram for histidine tagged plastocyanin (a) at AcBztacn modified gold/Zn electrode in 0.1 M phosphate buffer, with a scan rate of 20 mV/s (vs NHE) and histidine tagged bovine cytochrome P450c17 (b) at AcBztacn modified gold/Zn electrode in 0.1 M phosphate buffer, and the surfactant DDAB (didodecylammonium bromide), with a scan rate of 5 mV/s vs NHE.

We compared the electrochemical behaviour of *E. coli* thioredoxin specifically captured via a histidine-tag using the methods of the present invention with thioredoxin covalently immobilized on a SAM with random orientation. FIG. 3 illustrates typical cyclic voltammograms obtained at a gold electrode. The solid line represents an electrode modified using the procedure described in Example 1, leading to an oriented monolayer; the dashed line represents an electrode modified by coupling surface amines on the protein to the electrode, leading to a randomly oriented monolayer. The scan rates shown are a) 200 µV/s, b) 1 mV/s and c) 10 mV/s. 20 mM phosphate buffer, pH 7.0. We observed a superior electrochemical response using the oriented protein layer, with a faster electron transfer rate constant (more reversible redox signal) and an improved signal to background ratio.

Example 4

Surface Plasmon Resonance (SPR) Analysis of a Gold Chip Modified According to the Present Invention Compared with a Commercial BIAcore NTA Chip Other histidine tagged proteins that were immobilized included bovine cytochrome P450c17, *Synechocystis* plastocyanin and *Montipora efflorescens* green fluorescent protein (GFP).

BIAcore spectra were obtained on a BIAcore X analytical system using modified J1 (J1 is a plain gold surface) and NTA sensor chips (BIAcore AB, Uppsala, Sweden). The J1 chip was modified according to the methods described in Example 1, resulting in a 1-acetato-4-benzyl-1,4,7-triazacyclononane ("AcBztacn") chip, and the NTA chip was used as purchased. The running buffer was 10 mM HEPES, 150 mM NaCl, the activation buffer was 500 µM $NiCl_2$, 10 mM HEPES, 150 mM NaCl, the sample buffer was 30 µg/mL thioredoxin in 10 mM HEPES, 150 mM NaCl and the regeneration buffer was 350 mM EDTA, 10 mM HEPES, 150 mM NaCl (all at pH 7.4). All solutions were freshly prepared, degassed and filtered through a 0.2 µm Millipore filter. Oriented binding was evaluated by charging the chip with activating buffer (30 µL/min for 1 min) followed by sample buffer (30 µL/min for 1 min). The stability of the protein-chip interaction was monitored by passing running buffer (20 µL/min) over the surface and monitoring the sensorgram over time. The dissociation rate was determined as the percentage of original binding lost per minute across a period of between 2 and 14 h, assuming a linear decay. Non-specific protein binding was evaluated by injecting sample buffer before Ni activation, thus comparing the weakly attached protein material prior to activation of the chips by metal ions.

Figure 5:
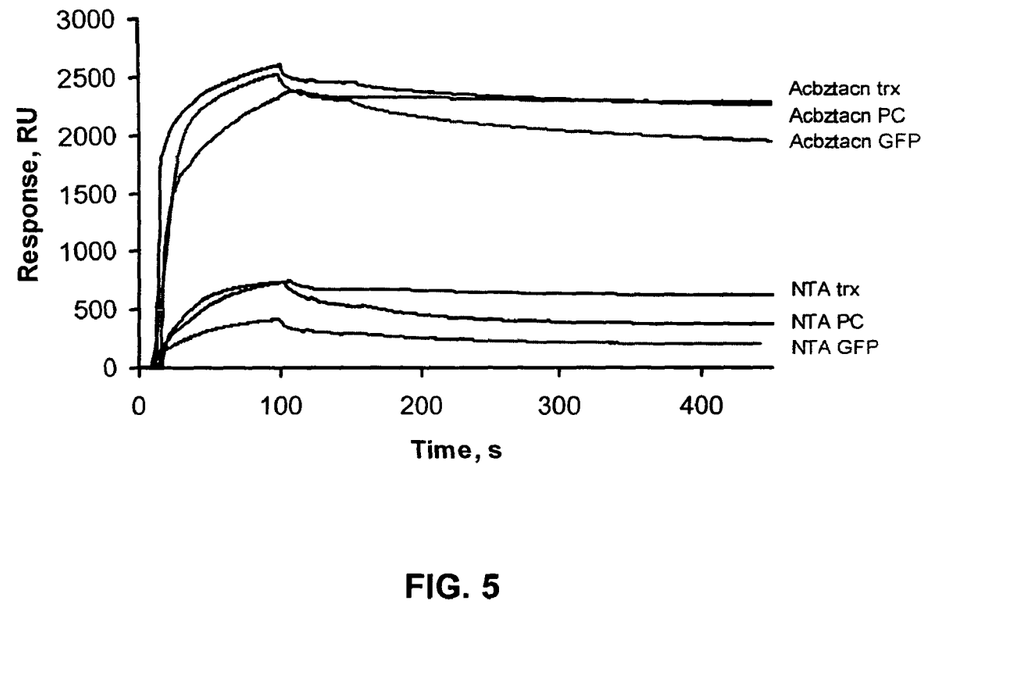
FIG. 5 shows binding of His-tagged thioredoxin, plastocyanin and green fluorescent protein to Acbztacn- and NTA-modified surfaces. Protein concentration is 30 µgmL$^{-1}$ in 10 mM HEPES, 150 mM NaCl, pH 7.4.

Protein binding to the chip was assessed using SPR, as shown in FIG. 5. We compared our AcBztacn electrode with the commercially available NTA chip from BIAcore for two proteins histidine-tagged thioredoxin and *Montipora efflorescens* green fluorescent protein (GFP (Table 1)). In particular, we examined the relative binding magnitude, stability (as assessed by protein dissociation) and the degree of non-specific binding of histidine-tagged thioredoxin and *Montipora efflorescens* green fluorescent protein (GFP). Despite a lower surface coverage, the AcBztacn modified surface displayed greater than five-fold increase in binding magnitude (Table 1) as assessed by the amount of bound protein to Ni-treated surface. The stability of the protein-Ni interaction was assessed by the rate of decay of the initial binding strength, as determined by the amount of protein dissociation after protein loading and expressed as the percentage of dissociation per minute. The AcBztacn-Ni-protein complex is eight times more stable than NTA-Ni-protein (Table 1). The AcBztacn electrode therefore has potential applications for long term biosensor use, with 50% of bound protein dissociated from the NTA chip in less than 40 min, compared with a loss of only 40% of total protein even after 15 h for the AcBztacn electrode (shown by a comparison of the dissociation rates in Table 1). Binding of protein prior to Ni ion activation was an order of magnitude greater for NTA, indicating that a component of non-specific binding occurs in the NTA chips. The increased binding of protein, improved stability and a reduction in non-specific binding indicates that the AcBztacn surface of the sensor chips of the present invention has superior qualities to this commercially-available system.

TABLE 1

|  | Ni—NTA | Ni—AcBztacn | Improvement Factor |
|---|---|---|---|
| Thioredoxin |  |  |  |
| Immobilized protein (RU) | 828 | 4504 | 5.4 |
| Dissociation rate (% of initial RU lost per min) | 1.7 | 0.2 | 8.5 |
| Non-specific protein binding (%) | 46.7 | 5.0 | 9.2 |
| Green Fluorescent Protein |  |  |  |
| Immobilized protein (RU) | 376 | 2325 | 6.2 |
| Dissociation rate (% of initial RU lost per min) | 7.6 | 0.9 | 8.4 |
| Non-specific protein binding (%) | 38 | 4 | 9.5 |

Finally, it is to be understood that various other modifications and/or alterations may be made without departing from the spirit of the present invention as outlined herein and as described in the claims appended hereto.

What is claimed is:

1. A biosensor comprising:
a solid support having a surface;
a plurality of linkers attached to the surface, wherein each linker includes a head group that is bound to the surface, and a multidentate macrocylic tail group comprising 1-acetato-4-benzyl-1,4,7-triazacyclononane chelated to a metal ion; and
a monolayer of molecules immobilised to the solid support by the plurality of linkers and having a binding affinity for an analyte, wherein each molecule of the monolayer contains a metal ion chelating tag that coordinates with the metal ion on a tail group of a linker, thereby holding a majority of the molecules of the monolayer in the same orientation with respect to the surface of the solid support.

2. The biosensor of claim 1 wherein the metal ion is selected from the group consisting of zinc, copper, cobalt, nickel, sodium, potassium, magnesium, calcium, and lithium.

3. The biosensor of claim 1 wherein the tag is a peptide chain containing one or more chelate forming amino acids independently selected from the group consisting of cysteine, lysine, histidine, and arginine.

4. The biosensor of claim 3 wherein the tag is a peptide containing three to six histidine residues.

5. The biosensor of claim 1 wherein the solid support is a noble metal selected from the group consisting of silver, gold, platinum, and palladium.

6. The biosensor of claim 1 wherein the linker includes a spacer between the head and tail groups.

7. The biosensor of claim 6 wherein the spacer is a carbon-based chain between the head and tail groups.

8. The biosensor of claim 7 wherein the carbon-based chain is two to fifteen atoms in length.

9. The biosensor of claim 8 wherein the carbon-based chain is two to six atoms in length.

10. The biosensor of claim 1 wherein the head group is sulfur, oxygen or selenium.

11. The biosensor of claim 1 wherein the monolayer comprises molecules of peptide or protein.

12. The biosensor of claim 11 wherein the tag is covalently bound to the protein at a position on the protein that is separated from the active site or recognition region of the protein.

* * * * *